United States Patent [19]
Gallagher

[11] Patent Number: 5,532,404
[45] Date of Patent: Jul. 2, 1996

[54] MONOMER RECOVERY PROCESS FOR CONTAMINATED POLYMERS

[75] Inventor: Francis G. Gallagher, Wilmington, Del.

[73] Assignee: E. I. du Pont de Nemours and Company, Wilmington, Del.

[21] Appl. No.: 250,391

[22] Filed: May 27, 1994

[51] Int. Cl.$^6$ .................................................. C07C 67/48
[52] U.S. Cl. ............................................ 560/78; 560/96
[58] Field of Search .................................. 560/78, 96

[56] References Cited

U.S. PATENT DOCUMENTS

| | | | |
|---|---|---|---|
| 2,884,443 | 4/1959 | Laudenbach et al. | 260/475 |
| 3,037,050 | 5/1962 | Helsenberg et al. | 260/475 |
| 3,321,510 | 5/1967 | Lotz et al. | 260/475 |
| 3,544,622 | 1/1970 | England | 260/515 |
| 3,776,945 | 12/1973 | Ligorati et al. | 260/475 D |
| 3,907,868 | 9/1975 | Currie et al. | 260/475 D |
| 3,952,053 | 4/1976 | Brown, Jr. et al. | 260/525 |
| 4,355,175 | 10/1982 | Pusztaszeri | 562/483 |
| 4,542,239 | 9/1985 | Lamparter et al. | 562/487 |
| 4,609,680 | 9/1986 | Fujita et al. | 521/48 |
| 5,051,528 | 9/1991 | Naujokas et al. | 560/78 |
| 5,298,530 | 3/1994 | Gamble et al. | 521/48.5 |
| 5,413,681 | 5/1995 | Tustin et al. | 203/80 |

FOREIGN PATENT DOCUMENTS

| | | | |
|---|---|---|---|
| 0484963 | 5/1992 | European Pat. Off. | C07C 69/82 |
| 54-84525 | 7/1979 | Japan | C07C 121/43 |
| 58-020951 | 4/1983 | Japan | C07C 69/82 |
| 1172997 | 12/1969 | United Kingdom | C07C 87/14 |

*Primary Examiner*—José G. Dees
*Assistant Examiner*—Rosalynd A. Williams

[57] ABSTRACT

An improved process for recovering reaction products from polymers such as polyesters or polyamides, especially those having a desired polymer level below about 98%. The process involves depolymerization and vapor phase extraction of monomers in the presence of a solid support.

20 Claims, No Drawings

MONOMER RECOVERY PROCESS FOR CONTAMINATED POLYMERS

BACKGROUND OF THE INVENTION

1. Field of the Invention

This invention relates to recovery of reaction products (i.e. monomers and other depolymerization products) from contaminated plastics. Specifically, this invention relates to processes for recovering monomers from polymers having a desired polymer content below about 98%.

2. Technical Background of the Invention

The inadequate treatment of waste which is landfilled, and the increasing percentage of nondegradable materials, including plastics, in municipal solid waste streams, have increased the cost of solid waste disposal and further stimulated public pressure to recycle nondegradable plastic material.

Over the years there have been many technological developments in the field of production and use of polymers. Various additives, modifiers, comonomers, copolymers, and fillers have been incorporated into polymers to improve characteristics such as strength and temperature resistance, and to thereby meet the needs of more specialized applications. Polymers have also been used in conjunction with other materials to make complex systems and composites where separation of the individual materials would be difficult. In addition to material added in the manufactured polymer, post-consumer solid waste usually contains contamination introduced during consumer use of the article or during the collection process. The presence of these contaminants, and materials incorporated during manufacture, have limited the effectiveness of post-consumer plastic recycling. The problem is one of initial low purity of the desired plastic and the necessity to process a wide range of other materials that may be present.

Polyesters and polyamides may be recycled by various methods to yield useful polymers, oligomers and monomers. Traditional chemical recovery techniques include hydrolysis, glycolysis and methanolysis for polyesters, and hydrolysis and ammonolysis for polyamides. For polyesters, these methods are most often combined with an initial depolymerization step, which is accomplished by heating and/or dissolving the polymer in oligomers, monomers (such as ethylene glycol), or water.

Hydrolysis involves treating the starting polymer with water and heat. Complete depolymerization will yield monomers (e.g., terephthalic acid (TPA) and ethylene glycol (EG) for polyethylene terephthalate (PET); and hexamethylene diamine (HMD) and adipic acid for nylon 6'6), which can then be polymerized. For PET, additional additives such as salts, NaOH, $H_2SO_4$, and $NH_3OH$, are sometimes used to enhance the process. See U.S. Pat. Nos. 4,355,175, 3,544,622, 3,952,053 and 4,542,239, respectively. Additionally, hydrolysis, specifically steam treatment, can be used in conjunction with other treatments discussed below, see U.S. Pat. No. 3,321,510.

Another recovery method for PET, glycolysis, is accomplished by using a glycol, e.g. ethylene glycol (EG) or butane diol (BDO), to break down the polymer. This has been done in the liquid phase, and usually employs heat and pressure. Glycolysis of PET with ethylene glycol yields bis-β-hydroxyethyl terephthalate (BHET) which is then usually filtered to remove impurities and polymerized, see U.S. Pat. No. 4,609,680. Glycolysis can be combined with a second step-like methanolysis, see U.S. Pat. No. 3,321,510.

The third method for polyesters, alcoholysis, e.g., methanolysis, breaks down the polymer back to its monomers. Conventional methanolysis generally operates using a polymer melt in which super heated methanol is bubbled through the mixture. See for example EPO Patent Application 0484963A3 and U.S. Pat. No. 5,051,528. Methanolysis can optionally include the use of catalysts to enhance the recovery rate, see, for example, U.S. Pat. Nos. 3,776,945 and 3,037,050, as well as the use of organic solvents, see U.S. Pat. No. 2,884,443. Methanolysis can be used in conjunction with various initial depolymerization methods, for example, dissolving the polymer in its oligomers, see U.S. Pat. No. 5,051,528; depolymerizing using EG, see Japanese Patent No. 58,020,951 B4; or depolymerizing using water, see U.S. Pat. No. 3,321,510. After alcoholysis of PET with methanol and recovering the monomers, an additional refining step may be used to separate and purify the DMT from EG. This can be done by precipitation, distillation, or cystallization.

For polyamides, ammonolysis can be used to break down the polymer back to monomers. For example, Japanese Patent Application Publication 54-84,525 (1979) describes a process to obtain the monomers 6-aminocapronitrile (6ACN) and caprolactam (CL) which is accomplished by treating molten polycaproamide (nylon 6) at elevated temperature and pressure with ammonia gas. British Patent 1,172,997 discloses the conversion of a polyamide into monomeric compounds by heating the polyamide (nylon 6 and nylon 6,6) with ammonia in the presence of hydrogen and a hydrogenation catalyst. With nylon 6,6 the monomers obtained are hexamethylene diamine (HMD) and hexamethyleneimine and a small amount of unidentified material. With nylon 6, the monomers obtained are HMD, hexamethyleneimine and N-(6-aminohexyl)-hexamethyleneimine.

SUMMARY OF THE INVENTION

This invention provides a process for recovering volatile reaction products (e.g. monomers and other depolymerization products) from a starting polymer charge or feed, wherein said polymer is a polyester or a polyamide having about 2% to 70% non-polymer contaminants, by weight, comprising:

(a) depolymerization of the polymer in the presence of a depolymerization agent to yield volatile reaction products;

(b) adding a vapor phase stripping agent, then vapor phase stripping the volatile reaction products, to yield a stripping agent/product distillate;

said depolymerization and vapor phase stripping carried out in the presence of a solid support, comprising from about 5% to about 99%, by weight, of the reaction mass, such that the reactor content geometry is substantially a suspended bed and the quantity and rate of recovery of reaction products is enhanced over that obtained in the absence of a solid support; and (c) leaving non-volatile residue materials with the support and recovering the reaction products from the stripping agent/product distillate.

The process is conducted within a temperature range of about 140° C. to about 350° C. Typical pressure for the reaction is below about 1000 psig (6894 kPa).

DETAILED DESCRIPTION OF THE INVENTION

The present invention addresses the following concerns:

(1) The desired polymer content of post consumer plastic varies and is typically less than about 98%, which decreases the yield of conventional recovery methods.

(2) The non-polymer contaminants vary in type and amount.

(3) To maximize the yield of recovered products while minimizing the quantity of byproduct, the residue following extraction of desired polymer optimally should have a low level (<50%) of desired polymer remaining.

(4) The polymer recovery process should be economical, minimizing the number of operations, supplemental material requirements and material movement.

The novelty of the applicants' solution to these concerns consists of the use of a solid support matrix to aid the depolymerization and vapor phase stripping of the monomers for polymer recycling, specifically including polyester and polyamide recycling.

Typical polyesters for treatment by the present process include, but are not limited to, polyethylene terephthalate (PET), polybutyleneterephthalate (PBT) and copolyesters. Typical polyamides include nylon 6 and nylon 66.

By "starting polymer feed or charge" (i.e. polymer contaminated with non-polymer contaminants) is meant any pre-consumer or post-consumer polymer having a desired polymer content below 98%. This includes polyesters, polyamides or any copolymer thereof. By non-polymer contaminants is meant any material that is not the desired polymer. This includes additives, modifiers, comonomers, copolymers, and fillers incorporated during polymer preparation; as well as other material and polymers incorporated during article construction and contamination introduced during use or during collection. The process described herein is suitable for processing non-polymer contamination levels of about 2% to about 70%, by weight of the starting charge or feed.

By "starting polymer charge" is meant starting polymer loaded in a single batch, while "starting polymer feed" refers to continuously feeding starting polymer to a reaction mass.

By "reaction products", herein is meant both the standard definition of monomer, a chemical compound that undergoes polymerization and makes up the basic repeating unit of a polymer, as well as other products obtained from depolymerization of a polymer, which can be chemically converted and subsequently polymerized. Examples of monomers that make up the basic repeating unit of a polymer are for polyesters, ethylene glycol and dimethylterephthalate, and for nylon, hexamethylenediamine. An example of another product obtained from depolymerization of a polymer, which can be easily converted to a monomer and then polymerized is adiponitrile obtained from nylon. For PET, reaction products include ethylene glycol (EG), dimethylterephthalate (DMT) and bis-β-hydroxyethylterephthalate (BHET). For nylon 6 and nylon 6,6, reaction products include hexamethylenediamine (HMD), 5-cyanovaleramide (CVAM), adiponitrile (ADN), caprolactam (CL), 6-aminocaproamide (ACAM) and 6-aminocapronitrile (6ACN).

By "volatile reaction products" is meant any monomer or product that has a sufficiently high vapor pressure to be stripped by a stripping gas at reaction temperatures and pressure. When operating continuously, the cost of recycling the stripping gas may be controlled by selecting operating conditions such that the concentration of reaction products in the stripping vapor is greater than about 1 weight % and preferably greater than about 10 weight %.

By "solid support" is meant a material, which is solid under reaction conditions, which expands the volume of the reaction media and provides additional reaction surface area to improve gas/polymer and gas/oligomer contacting, and to improve the rate or extent of depolymerization and stripping processes. The process of this invention requires about 5% to about 99% by weight, of support, per weight of reaction mass The "solid support" herein is preferably a plurality of inert particles which are solid under reaction conditions, which can be distributed substantially homogenously throughout the reaction mixture. Such particles provide a baffle-type system which supports the starting polymer and expands the volume of the reaction mixture. The expansion provides more gas/polymer and gas/oligomer contacting, thus improving the rate or extent of depolymerization and stripping processes.

In one embodiment of the invention, the supporting material is a component of the starting material, specifically glass fibers or flakes in engineering resin or composite systems. Solid supports which are components of the starting material can be described as having two general structures. The first is where the solid is "in contact with or connected to" the polymer, which means in physical contact with the polymer. This can include physical mixtures, blends and woven fabrics. A second structure is where the solid is intimately mixed or "fused" to the polymer, which means physically adhered to the polymer without adhesive, usually having been melted, such as in engineering polymer articles. The latter group presents a more difficult recycling problem than the former.

Alternatively, solid support material can be added to the reaction mixture to produce the same supporting effect. Suitable materials include (1) inorganic materials such as glass (e.g., silicon, boron), carbon fibers, ceramics, minerals (e.g., asbestos, mica, talc, wollastonite), (2) metals, (3) non-woven natural organic materials based on cellulose, hemicellulose, and lignin, among others, e.g., wood and (4) polymers that do not melt or significantly react (i.e., less than about 5 weight percent reacts at processing conditions) such as aramides, e.g., Kevlar® and Nomex® (DuPont, Wilmington, Del.).

By "depolymerization agent" is meant a solid, liquid or gas that will react with a repeat linkage, e.g., ester or amide linkages, to yield two product components, thus lowering the molecular weight and increasing the vapor pressure. For polyesters, the depolymerization agent can be a low molecular weight oligomer of a polyester, an alcohol, such as methanol, a monomer, an alkane diol, specifically ethylene glycol, an aromatic or aliphatic carboxylic acid, such as methyl benzoate, an aromatic or aliphatic dicarboxylic acid or corresponding ester, or water. By "oligomer" is meant a low molecular weight form of a given polymer. When water, oligomers, or some diols or dicarboxylic acids are used as the depolymerization agent, the initial product is not highly volatile. Thus, a second agent, such as alcohol or diol, is needed to yield more easily volatilized products. In these cases, the depolymerization is conducted in two steps, wherein the first step lowers the molecular weight and the second step yields a volatile monomer. For polyamides, the depolymerization agent may be methanol, ethylene glycol, oligomer of a polyamide, monomer, water or ammonia. Use of ammonia as a final depolymerization agent for polyamides is particularly advantageous because it produces volatile products which may be easily separated from the reaction mass.

By "stripping agent" is meant a material which is a gas at reaction temperature and pressure which is able to carry away the volatile products of the process and which will not retard the depolymerization reaction. The stripping gas may be the depolymerization agent itself as long as such depolymerization agent yields a volatile product, (for example alcohols and alkane diols for PET or ammonia for nylon) or an inert material, such as nitrogen. The stripping gas is passed through the reaction vessel and carries away the volatile monomers.

The method of this invention can be used to obtain a better recovery percentage of desired reaction products for these polymer materials than is obtainable through recovery methods that do not use applicants' solid support matrix. The present method is particularly suited for scrap resin with only modest desired polymer content, for example, glass fiber or metal reinforced engineering polymers, and for treating physical blends of post-consumer PET and polyethylene, which is common in plastics recycling. Additionally, PET by-product from commercial facilities can be treated effectively, as well as composite structures such as carpet and fabric.

Traditional methods of polymer recycling are not as efficient as the present process in situations where the starting materials have a low level of desired polymer content. Typically, the by-product stream in these methods contains a relatively high polymer and corresponding reaction product content, greater than about 50%, and therefore suffers the loss of valuable reaction products, as well as increasing by-product production. This outcome is compounded when the starting material is a highly fiber-filled polymer since it is even more difficult to separate the impurities from the polymer. The process of this invention, however, involving depolymerization to volatile reaction products and vapor phase stripping in the presence of a solid support matrix, facilitates separation of impurities from polymer, as the desired reaction products are easily carried away by the vapor flow and impurities are trapped and suspended in the solid support material.

The need for the present invention arises because, as the depolymerization step of conventional methods proceeds, the concentration of non-polymer contaminants increases, causing a viscosity increase in the reaction mixture. Gas/liquid contacting is then more difficult and the reaction rate becomes limited. This reaction mass viscosity increase is particularly high when there are present solids with high length to width ratios, approximately greater than 10. (See for example, Metzner, A. B., *Journal of Rheology*, Vol 19, 1985 Issue 6, P739). This occurs because conventional methods operate using a polymer melt system. As melt viscosity increases, the methanol cannot efficiently "bubble" through and adequately contact the polymer. See, for example, EPO Patent Application 0484963A3 and U.S. Pat. No. 5,051,528. Such conventional methods do not overcome the increasing viscosity problem, nor do they address how to handle high levels of solids and contaminants, while also maximizing yield of the desired polymer.

The increasing viscosity problem of conventional methods may be completely avoided, as evidenced by the invention herein, in which the vapor contacting area is maintained in a suspended bed with a supporting solid material, rather than as a liquid or melt. "Suspended bed" describes a reactor content geometry where a solid support is a continuous phase and has sufficient rigidity to maintain a porosity for gas passage, thus developing increased vapor contacting area. A suspended bed may have many phases present including gas, liquids of high and low viscosity, as well as solids.

The use of a solid support can maintain a suspended bed reactor content geometry. The solid support is functioning in a similar way to packing in a packed distillation column. Typical packings for such columns are rigid, inert particles. These particles are shaped to provide the maximum porosity possible, since the flow rate and separation efficiency of packed columns are directly dependent on the porosity. Most column packings are made of ceramics, metals, glass, and even unreactive polymers, since these materials are suitably rigid and inert. (See Ullman's Encyclopedia of Industrial Chemistry, Volume B3, Unit Operations II, Fifth Edition, VCH Publishers, NY (1988), pp. 4-82–84.) These materials have similarly been found suitable for the solid support of this invention.

By keeping the reaction mixture in a predominantly solid state, rather than maintaining it as a complete liquid or melt, with the supporting solid material present, a high surface area for gas/polymer interactions is maintained and subsequently gas/oligomer interactions occur.

The invention provides an improved method of recovering reaction products from polymer scrap resin by subjecting the scrap resin to a depolymerization agent and a vapor stripping agent in the presence of a supporting material, such that the resulting reaction products are removed from the reactor as a vapor and non-polymer contaminants remain with the supporting material. Subsequently the reaction products may be filtered or otherwise treated (e.g. using carbon adsorbers) to remove volatile non-polymer contaminants and recovered by conventional techniques, such as distillation or crystallization or directly repolymerized to a high molecular weight polymer. The residue consisting of solid support and non-polymer contaminants, may also be treated so that the solid support may be reused. Typical methods for such regeneration are pyrolysis or oxidation.

Determination of appropriate temperature and pressure conditions for the process of this invention is influenced by two factors: (1) the reaction rates to produce volatile reaction products and (2) the vapor pressures of the volatile reaction products, which is the driving force to remove the volatile reaction products in the vapor phase. Reaction rates are dependent on the specific reaction kinetics for the specific chemical reactions, thus a general statement about temperature and pressures is impractical. The use of catalysts can further complicate this issue. With regard to the removal of volatile reaction products in the vapor phase, basic engineering can be applied and temperature and pressure limits can be determined. For a specific reaction system, goal volatile reaction products can be identified. The least volatile reaction product, usually the one of highest molecular weight, must have a vapor pressure greater than about 0.2% of the total pressure of the system to be efficiently removed, preferably greater than 0.5% of the total pressure, and most preferably greater than about 2.0% of the total pressure. Although lower vapor pressure products may be removed using this invention, the cost of stripping agent recovery and recycle makes recovery of these materials expensive, and therefore only economical if they have a high value. The operating temperature will vary depending on the operating pressure and the partial pressure of the least volatile reaction product. Typically, for methanolysis of PET, the operating pressure can range from about 0 psig (6.9 kPa) to about 500 psig (3447 kPa), most preferably about 50 psig (345 kPa) to about 100 psig (689 kPa), and the operating temperature can range from about 140° C. to about 350° C., most preferably about 220° C. to about 300° C. For glycolysis of PET, the operating pressure can range from absolute vacuum to about 50 psig (345 kPa), preferably near atmospheric pressure, and the operating temperature can range from about 250° C. to about 350° C., preferably about 300° C.

Further, the method of this invention may be combined with other depolymerizing and recovery techniques as described in the technical background above. As discussed above, depolymerization of PET can be accomplished through the use of diols, dicarboxylic-acids and corresponding esters, monomers, monocarboxylic acids and corresponding esters, oligomers, water, alcohols, e.g., methanol, with optional catalysis. Recovery steps can include distillation, precipitation, filtration, carbon adsorption, crystallization, centrifugation, and subsequent repolymerization. To improve reaction rates, as an example, the steps of the proposed process could be combined with various catalysts and/or pretreatment steps, as described above.

In the process of the invention, the reactor is preferably stainless steel, suitable for pressure operation and equipped with an inlet dip tube, a thermocouple, a vapor vent and a heated jacket. When methanol is used as the depolymerization and stripping agent for polyesters, the reactor is typically operated at approximately 50 psi (345 kPa) and 220–250° C. Methanol which is fed to the reactor at approximately 300° C., is first vaporized in a high pressure evaporator and then heated in a superheater. The vapor stream product is a mixture of ethylene glycol, methanol and DMT, which can be subsequently separated by: (1) precipitation of DMT, (2) distillation, (3) partial distillation to extract methanol and then repolymerization of the mixture, or (4) filtration to extract undesirable precipitates.

The process of the invention can be practiced in a batch or continuous fashion. For example, the process may be batch, as described in the examples, or continuous if there is continuous feeding of the polymer and discharging of the residual solid from the reactor, similar to a rotary kiln and various continuous drying processes. Examples of batch or continuous equipment suitable for gas/solid contacting operations may be found in Perry, R. H. et al., *Chemical Engineer's Handbook, 6th Edition*, McGraw-Hill, Inc., 1984, Specifically, Chapter 20. "Solids Drying and Gas-Solid Systems" provides descriptions of equipment suitable for use in the process of this invention. Suitable equipment includes, but is not limited to, the following: batch furnaces, continuous tunnels, rotary dryers, agitated dryers, gravity dryers, and fluidized bed systems. Additionally, the process can be designed such that the depolymerization and stripping steps are accomplished sequentially. Batch processing can encompass pulsing or cycling the reaction pressure to achieve repetitive depolymerization and stripping steps. Other solid/gas contacting systems are also suitable for use in carrying out the process of this invention.

The depolymerization or pretreatment step may be accomplished with or without the presence of a solid support. The pretreatment step may be accomplished with a starting charge or feed that is a solid using conventional solid mixers as shown in Example 9, or a melt using polymer processing equipment. See, for example, Frades, Joel, *Plastic Engineer's Handbook, 4th Edition*, Van Nostrand Reinhold Company, 1976. Typical equipment may include intensive dry mixers, internal intensive batch mixers, continuous mixers and extruders.

The polymer charge or feed, as well as the solid support, may be preheated prior to entering the volatilization reactor to increase the rate of vaporization.

EXAMPLES

EXAMPLES 1–3: UNFILLED POLYETHYLENE TEREPHTHALATE HOMOPOLYMER

EXAMPLE 1

Polyester with Insulation Glass

This example was performed in a 1200 ml stainless steel reactor suitable for pressure operation and equipped with an inlet dip tube, a thermocouple, a vapor vent, and an electrically heated jacket. The vent from the reactor was connected to a recovery system.

The experiment was batch with respect to polymer and continuous with respect to the depolymerization and stripping agents. Methanol was used as the depolymerizing and stripping agent.

The reactor was charged with 200 g of commercial grade PET homopolymer (DuPont CRYSTAR® 1934, Wilmington, Del.; the same source was used for subsequent examples) and 67 g of insulation glass fibers (CTFSK, 1½ inch (3.81 cm), ¾ PCF FHC 25/50 R-5.2, Certain Teed Corp., Valley Forge, Pa.) which were physically blended. The vessel was heated using the electrically heated jacket.

When the internal temperature reached 180° C. hot methanol flow (about 300° C.) was fed into the reactor at about 10 ml/minute (measured as a liquid at room temperature). The methanol was provided from a reservoir, through a positive displacement pump, a steam jacketed evaporator and finally an electrically heated superheater. The vessel temperature rapidly increased and was maintained at goal conditions using the heated jacket. The maximum reaction temperature achieved was about 225° C., below the m.p. of PET but above the melting point of its reaction products. The extent of reaction was monitored by observing the rate of DMT collection. Methanol flow was maintained either for a fixed amount of time or until an observable drop in dimethylterephthalate collection was observed.

In this and the following examples, the reactor residue was weighed and analyzed for DMT and oligomer content as well as for inorganics. The amount of DMT and oligomer was determined by a % acetone insoluble test, since DMT and oligomers dissolve in acetone (up to a molecular weight, Mn, of about 225), but high molecular weight polymers do not. The glass and inorganic content were determined by % ash. From this data, the PET lost in the by-product can be determined. The theoretical residue was calculated from the known composition of the starting material, being the amount of non-polyester material. If the composition was not known, it was measured as described below. The percent polymer conversion is calculated as follows:

$$\% \text{ Polymer Conversion} = \frac{(\text{Total Weight Charged} - \text{actual residue})}{(\text{Total Weight Charged} - \text{theoretical residue})} \times 100$$

The total weight charged does not include ethylene glycol and catalyst added during pretreatment. A summary of key process variables and sample analysis is presented in Table 1.

The resulting residue clearly demonstrated two distinct phases. A top phase above the dip tube exit that was predominantly glass, and a bottom phase that was below the dip tube exit and predominantly oligomer. After about 11 hours, 55% of the PET was converted.

EXAMPLE 2

PET with Added Glass Bundles

The reactor set-up and the general process employed were the same as that used in Example 1. The reactor was charged with 200 g of PET and 200 g of glass fiber bundles (½ inch (3.81 cm) chopped glass, Owens/Corning Fiberglas Corp., Toledo, Ohio) which were physically blended. The resulting residue clearly demonstrated two distinct phases. A top phase above the dip tube exit that was predominantly glass, and a bottom phase that was below the dip tube exit and predominantly oligomer. After 12.5 hours, 52% of the PET was converted.

Residual material was recovered from the reactor and analyzed for ash content and % insolubles. Results are shown in Table 1.

EXAMPLE 3

PET with added Glass Fibers

The reactor set-up and the general process employed were the same as that used in Example 1. 200 g of PET and 100 g of finely divided glass fibers (recovered from Examples 6–11) were physically blended as they were charged to the reactor.

Residual material was recovered from the reactor and analyzed for ash content and % insolubles. Complete conversion of the PET was achieved in 11 hours. Results are shown in Table 1.

COMPARATIVE EXAMPLE A

PET without Solid Support

The reactor set-up and the general process employed were the same as that used in Example 1. The reactor was charged with 200 g of commercial grade PET as unprocessed pellets. The reactor operated at about 221° C. (below the melting point of PET but above the melting point of its monomers) while hot methanol was passed through the polymer.

Residual material was recovered from the reactor and analyzed for ash content and % insolubles. Results, shown in Table 1, indicate that the polymer conversion was not as high as that demonstrated in Examples 1–3.

It should be noted that a limiting feature of the equipment used in the examples of the invention herein, was that the reactor dip tube, used for the introduction of methanol, did not extend to the bottom of the reactor. Approximately 160 ml of reactor volume is below the dip tube. Thus, in runs made without a solid support matrix present, about 170 g of polymer may not be effectively contacted with methanol; the methanol only sweeping past the surface.

SUMMARY: EXAMPLES 1–3

The introduction of glass fibers in Examples 1–3 increased the conversion of PET to volatile monomers versus Example A where no glass was present. Part of the striking improvement was due to specific reactor geometry (see Note in Ex. A), but this cannot explain the 100% conversion in Example 3.

EXAMPLES 4–5

UNFILLED PET WITH POLYETHYLENE

EXAMPLE 4

Polyethylene (PE)/PET Mixture with added Glass Fibers

The reactor set-up and the general process employed were the same as that used in Example 1. In this example, 100 g PE, 100 g PET and 100 g of glass (recovered from Examples 6–11) were charged to the reactor. Complete conversion of the PET was achieved in 6 hours. The residual appearance was uniform glass with concentrated areas of PE distributed uniformly. Due to the higher PE levels the residue was not free flowing.

Residual material was recovered from the reactor and analyzed for ash content and % insolubles. Results are shown in Table 1.

EXAMPLE 5

PE/PET Mixture with added Glass Fibers

The reactor set-up and the general process employed were the same as that used in Example 1. In this example, 40 g PE, 160 g PET and 100 g of glass (recovered from Examples 6–11) were charged to the reactor. Complete conversion of PET was achieved in 5 hours. The residue appearance was uniform free flowing glass with concentrated areas of PE that were distributed uniformly.

Residual material was recovered from the reactor and analyzed for ash content and % insolubles. Results are shown in Table 1.

COMPARATIVE EXAMPLE B

Polyethylene (PE)/PET Mixture

The reactor set-up and the general process employed were the same as that used in Example 1. In this example, 40 g polyethylene (Oxychem, Dallas, Tex.) and 160 g PET were charged to the reactor that was heated to 282° C. with 10 ml/min methanol flow. After 9 hours, 170 grams of material remained. The resulting residue clearly demonstrated two distinct phases. A top phase was predominantly PE and a bottom phase was predominantly polyester.

Residual material was recovered from the reactor and analyzed for ash content and % insolubles. Results, shown in Table 1, indicate that the polymer conversion was not as good as Example 5, which used the same polymer mixture but incorporated a solid support.

COMPARATIVE EXAMPLE C

PE/PET Mixture

The reactor set-up and the general process employed were the same as that used in Example 1. In this example, 100 g PE and 100 g PET were charged to the reactor that was heated to 282° C. with 10 ml/min methanol flow. After 9 hours, 196 g remain. Again the two phases were observed, a PE top phase and a bottom polyester phase.

Residual material was recovered from the reactor and analyzed for ash content and % insolubles. Results, shown in Table 1, indicate that the polymer conversion was not as good as Example 4, which used the same polymer mixture but incorporated a solid support.

SUMMARY EXAMPLES 4–5

Introduction of glass fibers in Examples 4 and 5 improve conversion of polyester to monomers, compared to Comparative Examples B and C.

EXAMPLES 6–11

FILLED PET—WITH VARIOUS PRE-TREATMENTS AND PROCESS CONDITIONS

EXAMPLE 6

Filled PET

The reactor set-up and the general process employed were the same as that used in Example 1. This example employs PET in which the support material is part of the starting material. Experimental polyester/glass composite parts, containing about 72% PET, 25% chopped glass fibers (same fibers as Example 2), and the balance being modifiers, were ground and screened through a ⅜ inch screen. 400 grams of the ground material were charged to the reactor. After 16 hours, 170 grams of residue were extracted and was analyzed for ash content and % insolubles. Results are shown in Table 1.

EXAMPLE 7

Filled Polyester with Ethylene Glycol Pretreatment

The reactor set-up and the general process employed were the same as that used in Example 1. 400 grams of the ground material (from Example 6) was physically blended with 32 grams of ethylene glycol (Polyester Grade Product Code 35227, Union Carbide Chemicals and Plastics Co., Inc., Danbury, Conn.) prior to charging the reactor. Standard heat-up and operating procedures were followed. After 12 hours of operation, 138 grams of residue were extracted and analyzed for ash content and insolubles. Results are shown in Table 1.

EXAMPLE 8

Example 7 Treatment with Catalyst Solution

The reactor set-up and the general process employed were the same as that used in Example 1. 400 grams of the ground material (from Example 6) was physically blended with 33 grams of ethylene glycol and tetra butyl titanate (TBT) (2.5%) (DuPont TYZOR® TBT, Wilmington, Del.) solution prior to charging the reactor. Standard heat-up and operating procedures were followed. After 7 hours of operation, 113 grams of residue remained which were found to contain 90.8% ash.

Residual material was also analyzed for % insolubles. Results are shown in Table 1.

EXAMPLE 9

Example 8 Treatment with Preheating

The reactor set-up and the general process employed were the same as that used in Example 1. 400 grams of the ground material (from Example 6) were physically blended with 33 grams of ethylene glycol/TBT catalyst (2.5%) solution. The mixture was then pretreated by placing in a rotary evaporator and gently tumbled while heating to 150° C. and maintaining that temperature for 4 hours. The mixture was then charged to the reactor. Standard heat-up and operating procedures were followed. After 5 hours of operation, 115 g of residue remained, containing 90.2% ash.

Residual material was also analyzed for % insolubles. Results are shown in Table 1.

EXAMPLE 10

Example 8 Treatment with increased MeOH Flow

The reactor set-up and the general process employed were the same as that used in Example 1. Here, Example 8 was repeated except the methanol flow rate was increased to 20 ml/min. Reaction was completed in 4 hours with similar extraction and ash content.

Residual material was recovered from the reactor and analyzed for ash content and % insolubles. Results are shown in Table 1.

EXAMPLE 11

Example 8 at 100 psi

The reactor set-up and the general process employed were the same as that used in Example 1. Here, Example 8 was repeated but the pressure was increased to 100 psi. After 7 hours of operation, 110 grams of residue remained which were found to contain 87% ash.

Residual material was also analyzed for % insolubles. Results are shown in Table 1.

SUMMARY: EXAMPLES 6–11

Examples 6 through 11 demonstrate the advantage of treating the polymer to initiate depolymerization. Introduction of ethylene glycol and catalyst accelerates the depolymerization process. The higher methanol flow rate in Example 10 increased the stripping capacity of the system. Operating at a higher pressure improved conversion slightly.

EXAMPLES 12–15

FILLED AND UNFILLED PET MIXTURES WITH CATALYST TREATMENT

EXAMPLE 12

Filled PET/Unfilled, Contaminated PET with Catalyst Solution

The reactor set-up and the general process employed were the same as that used in Example 1. 100 g of ground material (from Example 6), 225 g PET and 12 g ethylene glycol/TBT catalyst solution (5% catalyst) were physically blended then charged to the reactor. After hours, essentially all of the polyester was extracted.

Residual material was recovered from the reactor and analyzed for ash content and % insolubles. Ash content of the residue was found to be 88%. Results are shown in Table 1.

EXAMPLE 13

Filled PET/Unfilled PET with Catalyst Solution

The reactor set-up and the general process employed were the same as that used in Example 1. 200 g ground material (from Example 6), 200 g PET and 16 g ethylene glycol/TBT catalyst solution (5%) were charged to the reactor. After 8 hours, essentially all of the polyester was extracted.

Residual material was recovered from the reactor and analyzed for ash content and % insolubles. Ash content of the residue was 90.3%. Results are shown in Table 1.

EXAMPLE 14

Filled PET/PET Oligomer with Catalyst Solution

The reactor set-up and the general process employed were the same as that used in Example 1. 280 g of ground material (from Example 6), 90 g of PET oligomer from a commercial facility (degree of polymerization, $D_p$, was about 5–10) and 12 g TBT catalyst solution (5%) were charged to the reactor. After 9 hours, essentially all of the polyester was extracted.

Residual material was recovered from the reactor and analyzed for ash content and % insolubles. Ash content of residue was found to be 90.8%. Results are shown in Table 1.

COMPARATIVE EXAMPLE D

PET Oligomer with Catalyst Solution

The reactor set-up and the general process employed were the same as that used in Example 1. 300 grams of PET oligomer (same as Example 14) and 12 g of ethylene glycol/TBT catalyst (5%) solution were charged to the reactor. After 11 hours, all of the charged material was reacted. No residual material was left.

EXAMPLE 15

Filled PET/PET By-product with Catalyst Solution

The reactor set-up and the general process employed were the same as that used in Example 1. 100 g of ground material (from Example 6), 225 g of a PET residue from a large scale methanolysis Market Development Facility (MDF) and 12 g ethylene glycol/TBT catalyst solution (5%) were charged to the reactor. After 11 hours, most of the PET was extracted.

Residual material was recovered from the reactor and analyzed for ash content and % insolubles. Ash content of residue was found to be 83.5%. Results are shown in Table 1.

COMPARATIVE EXAMPLE E

PET By-product with Catalyst Solution

The reactor set-up and the general process employed were the same as that used in Example 1. 300 grams of a PET residue from a Market Development Facility (MDF) and 12 g of ethylene glycol/TBT catalyst (5%) solution were charged to the reactor. After 12 hours the majority of the polyester was extracted.

Residual material was recovered from the reactor and analyzed for ash content and % insolubles. Results are shown in Table 1.

SUMMARY: EXAMPLES 12–15

Examples 12 through 15 demonstrate using glass filled PET as a support material to recover other PET. Example 12 and 13 demonstrate essentially complete conversion of PET versus Example A, where only 14% was converted. In Example 14, a low molecular weight oligomer was recovered faster than in Example D. It is interesting to note by comparison that in Example D the oligomer was completely converted, while Example A, the high molecular weight polymer, was not. This demonstrates that reducing the initial molecular weight is advantageous. In Example 15, additional monomers were recovered from residue obtained from a liquid phase methanoloysis facility. When the residue was methanolysized separately in Example E, a viscous tar residue was obtained at low yields.

EXAMPLE 16

PBT with Glass

The reactor set-up and the general process employed were the same as that used in Example 1. In this example, 300 g polybutyleneterephthalate and glass (50/50 blend of Celanese 6407 and 6500, Hoechst Celanese Corp., Chatham, N.J.), and 24.8 g of EG/TBT catalyst (2.5%) solution were charged to the reactor.

Residual material was recovered from the reactor and analyzed for ash content and % insolubles. Results are shown in Table 1.

EXAMPLES 17–20

USE OF VARIOUS STRIPPING AGENTS

EXAMPLE 17

Ethylene Glycol as Stripping Agent

The reactor set-up and the general process employed were the same as that used in Example 1. In this example, ethylene glycol was used as a depolymerizing and stripping agent. The volatile component generated in this example is bis-$\beta$-hydroxyethylterephthalate. 100 grams of ground material (from Example 6) was charged to the reactor. Reactor pressure was set at 0 PSIG. Ethylene glycol was fed at 10 ml/min when the reactor temperature reached 220° C. Heating was continued to 296° C. Conditions were held for 13 hours. Residual material was recovered from the reactor and analyzed for ash content and % insolubles. Results are shown in Table 1.

EXAMPLE 18

Example 21 Treatment with N2 added for Stripping

Example 17 was repeated with nitrogen added to assist with the stripping. 100 grams of ground material (from Example 6) was charged to the reactor. Reactor pressure was set at 0 PSIG. Ethylene glycol was fed at 10 ml/min (measured at ambient conditions) when the reactor temperature reached 220° C. Nitrogen was fed at 140 ml/min, measured at ambient conditions. Conditions were held for 12 hours.

Residual material was recovered from the reactor and analyzed for ash content and % insolubles. Results are shown in Table 1.

EXAMPLE 19

MeOH/Ethylene Glycol Mixture as Stripping Agent

The reactor set-up and the general process employed were the same as that used in Example 1. In this example, a 90/10 mixture of ethylene glycol and methanol was used as the depolymerization and stripping agent. The volatile components generated in this example are DMT, EG and bis-$\beta$-hydroxyethyl terephthalate. 400 grams of ground material (from Example 6) were charged to the reactor. Reactor pressure was set at 50 PSIG. The methanol/ethylene glycol mixture was fed at 10 ml/min when the reactor temperature reached 225° C. The maximum reaction temperature reached was 236° C. and conditions were held for 12 hours.

Residual material was recovered from the reactor and analyzed for ash content and % insolubles. Results are shown in Table 1.

EXAMPLE 20

Example 20 at Higher Temperature

The reactor set-up and the general process employed were the same as that used in Example 1. In this example, Example 19 was repeated but the maximum reaction temperature reached was 287° C. and conditions were held for 12 hours.

Residual material was recovered from the reactor and analyzed for ash content and % insolubles. Results are shown in Table 1.

EXAMPLE 21

Two-step Stripping - EG then Methanol

The reactor set-up and the general process employed were the same as that used in Example 1. In this example, Example 8 was repeated but stripping was accomplished by first feeding EG at 5 ml/min for 20 minutes, followed by methanol at 10 ml/min for the remainder of 9 hours. A slight improvement in DMT recovery rate was achieved over Example 8.

Residual material was recovered from the reactor and analyzed for ash content and % insolubles. Results are shown in Table 1.

TABLE 1

| | | | | PERCENTAGE POLYMER CONVERSION (All runs at 10 ml MeOH/min, 50 psig, unless noted) | | | | | |
|---|---|---|---|---|---|---|---|---|---|
| | MeOH | Max | Total | Theoret. | Actual | | Residue analysis | | |
| EX. | Flow (hrs) | Temp (°C.) | Charge* (grams) | Residue (grams) | Residue (grams) | % Polymer Conversion | % ash | % acetone insolub. | Charge Description |
| 1 | 11 | 234 | 267 | 67 | 157 | 55 | NA | NA | PET & INSULATION GLASS |
| 2 | 12.5 | 230 | 400 | 200 | 296 | 52 | 72 | 79.7 | PET & GLASS BUNDLES |

TABLE 1-continued

PERCENTAGE POLYMER CONVERSION
(All runs at 10 ml MeOH/min, 50 psig, unless noted)

| EX. | MeOH Flow (hrs) | Max Temp (°C.) | Total Charge* (grams) | Theoret. Residue (grams) | Actual Residue (grams) | % Polymer Conversion | Residue analysis % ash | Residue analysis % acetone insolub. | Charge Description |
|---|---|---|---|---|---|---|---|---|---|
| 3 | 11 | 226 | 300 | 100 | 99 | 100 | 90.56 | 99.3 | PET & RECOVERED GLASS |
| A | 8 | 221 | 200 | 0.2 | 173 | 14 | 0 | 84.5 | PET |
| 4 | 6 | 287 | 300 | 200 | 195 | 105 | 90.26 | 99.1 | 100PE/100PET/100R GLASS |
| 5 | 5 | 280 | 300 | 140 | 136 | 102 | 88.55 | 98.5 | 40PE/160PET/100R GLASS |
| B | 9 | 282 | 200 | 40 | 170 | 19 | 0.19 | 99 | 40PE/160PET |
| C | 9 | 282 | 200 | 100 | 196 | 4 | 0 | 99.4 | 100PE/100PET |
| 6 | 16 | 227 | 400 | 112 | 170 | 80 | 64.04 | 82.08 | Ground Composite |
| 7 | 12 | 227 | 400 | 112 | 138 | 91 | 76.68 | 88.72 | Ex. 6 & EG |
| 8 | 7 | 233 | 400 | 112 | 113 | 100 | 90.84 | 99.51 | Ex. 6 & EG & TBT |
| 9 | 5 | 233 | 400 | 112 | 115 | 99 | 90.24 | 99.29 | Ex. 6 & EG & TBT-PRETREAT |
| 10 | 4 | 241 | 400 | 112 | 104 | 103 | 89.39 | 99.36 | Ex. 6 & EG & TBT-20 CC/MIN |
| 11 | 7 | 248 | 400 | 112 | 110 | 100 | 87.19 | 99.95 | Ex. 6 + EG + TBT-100 PSI |
| 12 | 11 | 227 | 325 | 28 | 29 | 100 | 88.12 | 98.89 | 100 Ex. 6/225PET/EG + TBT |
| 13 | 8 | 227 | 400 | 56 | 61 | 99 | 90.28 | 99.3 | 200 Ex. 6/200PET/EG/TBT |
| 14 | 9 | 228 | 370 | 78 | 63 | 105 | 90.86 | 99.1 | 280 Ex. 6/90OH/EG/TBT |
| D | 11 | 225 | 300 | 0.3 | 0 | 100 | N/A | N/A | 300OH/EG/TBT |
| 15 | 11 | 230 | 325 | 50 | 38.5 | 104 | 83.5 | 94.6 | 100 Ex. 6/225MDF/EG/TBT |
| E | 12 | 228 | 300 | 30 | 100 | 75 | 1.34 | 16.64 | 300MDF/EG/TBT |
| 16 | 12 | 267 | 300 | 99.3 | 103 | 98 | 84.6 | 99.1 | PBT(GLASS)/EG/TBT |
| 17 | 13 | 296 | 100 | 28 | 48 | 72 | 64.86 | 99.6 | 10 cc EG/Ex. 6 0 psig |
| 18 | 12 | 302 | 100 | 28 | 39 | 85 | 60.9 | 99.5 | 10 cc EG-N₂/Ex. 6 0 psig |
| 19 | 12 | 236 | 400 | 112 | 229 | 59 | 44.96 | 73.2 | 90/10 MeOH/EG/Ex. 6 |
| 20 | 12 | 287 | 400 | 112 | 110.4 | 100 | 89.56 | 99.1 | 90/10 MeOH/EG/Ex. 6 |
| 21 | 9 | 235 | 400 | 112 | 112 | 100 | 86.6 | 99.2 | 400 Ex. 6/EG/TBT EG then MeOH |

*Excluding ethylene glycol and catalyst added during pretreatment

DETERMINATION OF THEORETICAL RESIDUE

For the most part theoretical residue was determined from the known composition of a particular sample (see Example 1). In situations where the composition was not known, the following method was used to estimate theoretical residue.

Into a 400 cc stainless steel vessel designed for high pressure and temperature was placed 237 grams of methanol and 12 grams of polymer and 0.05 g TBT catalyst. Using an external electric heater the vessel was heated to 250° C. and maintained at this temperature for 2 hours. Pressure in the vessel was allowed to build without venting (about 1400 PSIG). The vessel was allowed to cool to room temperature and was discharged.

The resulting suspension was filtered to collect the solids. (At room temperature DMT has a solubility in methanol of about 0.7% (wt) and ethylene glycol is fully soluble. The solubility of DMT in mixtures of methanol and ethylene glycol is slightly higher.)

The solids were dried and the dry weight was noted. At this point most of the solids are DMT.

The dissolved in acetone at a 2% level. DMT and oligomers (up to about 225 Mn) are soluble in acetone at room temperature. This solution was then filtered and the resulting solids are dried and weighed. Any residue collected at this point was not considered to be a polyester. This residue amount is considered to be "theoretical residue" for the polymer.

This "theoretical residue" estimate is conservatively low since some additives and modifiers are soluble in methanol or acetone and are thus not included in the estimate. However, these additives and modifiers may remain with the residue during methanolysis with vapor phase separation of reaction products.

To gain additional understanding, the acetone insoluble residue is ashed to determine inorganic content.

I claim:

1. A process for recovering reaction products from a reaction mass that comprises a starting polymer, wherein said polymer is a polyester or polyamide having about 2% to 70% by weight non-polymer contaminants, which process comprises:

(a) depolymerizing the polymer by means of a depolymerizing agent to yield volatile reaction products;

(b) vapor-phase stripping the volatile reaction products to yield a stripping-agent/product distillate;

wherein said depolymerization and vapor-phase stripping is carried out in the presence of a solid support that comprises from about 5% to 99% by weight of the reaction mass, which solid support is solid under the conditions of steps (a) and (b), such that a suspended bed is formed and the quantity and rate of recovery of reaction products is enhanced over that obtained in the absence of said solid support; and (c) recovering the reaction products from the stripping-agent/product distillate while leaving non-volatile residue material with the support material.

2. The process of claim 1 wherein the depolymerization agent is selected from the group consisting of an oligomer of a polyester, a polyamide, an alcohol, an alkane diol, an aromatic or aliphatic carboxylic acid or a corresponding ester, an aromatic or aliphatic dicarboxylic acid or a corresponding ester, ammonia, amine, diamine and water.

3. The process of claim 2 wherein said depolymerization is conducted within a temperature range of 140° C. to 350° C.

4. The process of claim 3 wherein the depolymerization step is conducted at a pressure of less than about 1000 psig.

5. The process of claim 4 wherein the stripping gas is selected from the group consisting of nitrogen, alcohol, alkane diols and ammonia.

6. The process of claim 5 wherein the solid support is a material selected from the group consisting of glass, carbon fibers, minerals, metals, ceramics, wood, aramid polymer, and non-depolymerizable residual polymer.

7. The process of claim 6 wherein the starting charge or feed is a polyester, wherein the depolymerizing agent and the stripping agent are methanol, wherein the temperature is about 220° C. to about 300° C. and wherein the pressure is 0 psig to about 200 psig.

8. The process of claim 6 carried out as a batch process.

9. The process of claim 7 carried out as a batch process.

10. The process of claim 6 carried out as a continuous process.

11. The process of claim 7 carried out as a continuous process.

12. The process of claim 6 wherein the solid support is a component of the starting charge or feed.

13. The process of claim 7 wherein the solid support is a component of the starting charge or feed.

14. The process of claim 12 wherein the solid support is fused to the polyester or polyamide.

15. The process of claim 13 wherein the solid support is fused to the polyester.

16. The process of claim 6 wherein the solid support is added to the starting polymer charge or feed.

17. The process of claim 7 wherein the solid support is added to the starting polymer charge.

18. The process of claim 1 wherein the solid support is preheated.

19. The process of claim 10 wherein the continuous process treats the starting charge in sequential steps of depolymerization followed by stripping.

20. A process for recovering reaction products from a reaction mass that comprises a starting polymer, wherein said polymer is a polyester or polyamide having about 2% to 70% by weight non-polymer contaminants, which process comprises:

(a) depolymerizing the polymer by means of a depolymerizing agent to yield volatile reaction products;

(b) vapor-phase stripping the volatile reaction products to yield a stripping-agent/product distillate;

wherein said depolymerization and vapor-phase stripping is carried out in the presence of a support material selected from the group consisting of glass, carbon fiber, mineral, metal, ceramic, wood, aramid, and non-depolymerized residual polymer, which support material comprises from about 5% to 99% by weight of the reaction mass, which support material is solid under the conditions of steps (a) and (b), such that a suspended bed is formed in which the support material provides porosity for gas passage and surface area for gas/polymer and gas/oligomer contacting, thereby enhancing the quantity and rate of recovery of reaction products over that obtained in the absence of said support material; and (c) recovering the reaction products from the stripping-agent/product distillate while leaving non-volatile residue material with the support material.

\* \* \* \* \*